United States Patent

Rinaldi et al.

[11] Patent Number: 5,919,728
[45] Date of Patent: Jul. 6, 1999

[54] CATALYST FOR THE FLUORINATION OF HALOGENATED HYDROCARBONS

[75] Inventors: Francesco Rinaldi, Padova; Paolo Cuzzato, Treviso; Letanzio Bragante, Albignasego, all of Italy

[73] Assignee: Ausimont S.P.A., Milan, Italy

[21] Appl. No.: 08/843,356

[22] Filed: Apr. 15, 1997

[30] Foreign Application Priority Data

Apr. 17, 1996 [IT] Italy .............................. MI96A0732 U
Mar. 21, 1997 [IT] Italy .............................. MI97A0655 U

[51] Int. Cl.[6] .............................. B01J 23/26; C07C 19/08
[52] U.S. Cl. .................. 502/305; 502/306; 502/308; 502/309; 502/319; 570/165; 570/169; 570/170
[58] Field of Search ..................... 502/325, 226, 502/228, 305, 306, 308, 309, 319; 570/169, 168, 165

[56] References Cited

U.S. PATENT DOCUMENTS

| | | | |
|---|---|---|---|
| 4,547,483 | 10/1985 | Muller | 502/226 |
| 5,600,039 | 2/1997 | Galland et al. | 570/169 |
| 5,616,820 | 4/1997 | Cheminal et al. | 570/169 |

FOREIGN PATENT DOCUMENTS

| | | |
|---|---|---|
| 2025145 | 3/1991 | Canada . |
| A0554165 | 8/1993 | European Pat. Off. . |
| 57-197233 | 12/1982 | Japan . |

OTHER PUBLICATIONS

Patent Abstracts of Japan, vol. 007, No. 046 (C–153), Feb. 23, 1983 and JP 57 197233 A (Asahi Glass KK), Dec. 3, 1982.

*Primary Examiner*—Ngoc-Yen Nguyen
*Attorney, Agent, or Firm*—Nikaido Marmelstein Murray & Oram, LLP.

[57] ABSTRACT

A fluorination catalyst based on of an amorphous Cr (III) compound and on a compound of another metal selected from Mg, Ca, Sr, Ba, Sc, Ti and Zr, wherein the atomic ratio of Cr/other metal is between 50:1 and 1:1, said compounds are supported on a $AlF_3$ support and being prepared by impregnating the support with a concentrated aqueous solution containing a soluble Cr (III) salt and a soluble salt of the other metal. The catalyst can be used in gaseous phase reactions.

10 Claims, No Drawings

CATALYST FOR THE FLUORINATION OF HALOGENATED HYDROCARBONS

BACKGROUND OF THE INVENTION

1. Field of the Invention

The present invention refers to a fluorination catalyst based on an amorphous Cr (III) compound and on a compound of another metal of the 2a, 3a and 4b groups of the periodic system, preferably Mg or Ca, supported on $AlF_3$ or fluorinated alumina, having an atomic ratio Cr/other metal higher than or equal to 1.

2. Description of Related Art

Such catalyst results particularly suitable in the fluorination in gaseous phase at atmospheric pressure of halogenated hydrocarbons with HF, in particular in the fluorination of $CF_3CH_2Cl$ to $CF_3CH_2F$, perchloroethylene (PCE) to $CF_3CHCl_2$, $CF_3CHClF$, $CF_3CHF_2$ (HCFC 123, HCFC 124, HFC 125 respectively), with high selectivity, efficiency and life-time.

The fluorination catalysts based on Cr (III) compounds, preferably supported on alumina, fluorinated alumina, aluminum trifluoride or carbon, are known in the art and industrially used for preparing HCFC and HFC not harmful for the ozone layer.

However such chromium catalysts have the drawback to cause also secondary reactions which lead to the formation of very undesirable by-products.

For instance, in case of fluorination of $CF_3CH_2Cl$ (HCFC-133a) to $CF_3CH_2F$ (HFC-134a), it is also obtained the formation of $CF_2=CHCl$ (HCFC-1122) which is not only toxic but is also difficult to be separated from 134a, requiring to this purpose further expensive purification processes such as those described in U.S. Pat. No. 5,475,168.

In the case of preparation of HFC-125, undesirable amounts of CFC-115 are obtained, said CFC being very difficult to separate from HFC-125 (see U.S. Pat. No. 5,087,329).

Moreover said Cr catalysts tend to deactivate since, during the use, there are deposited on their surfaces carbonaceous and/or oligomeric residues deriving from cracking and/or oligomerization of the organic compounds put to react or formed during the reaction, in particular of the unsaturated ones.

In order to be able to reactivate the catalyst it was therefore necessary to stop at intervals the manufacturing process to proceed to the catalyst regeneration, generally by oxidation with air at high temperatures of the carbonaceous deposits.

To overcome such drawback it is known in the prior art to add to the reaction mixture small amounts of oxygen (see e.g.

WO 90/08755). This addition of oxygen, while effective in sustaining the catalytic activity, has nevertheless two major drawbacks: the formation of halogenated epoxides, dangerously unstable, and the reaction of oxygen with the HCl which is formed in the main reaction, to give molecular chlorine which in turn reacts with the HFC/HCFCs forming CFCs that contaminate the desired products.

$$2\ RCHX_2 + 2\ HCl + O \rightarrow 2\ RCX_2Cl + H_2O$$

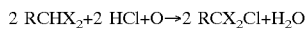

(X=F, Cl; R=halogenated alkyl)

The CFCs, as widely known, cannot be discharged into the atmosphere because of their impact on the ozone layer, and must thus be properly disposed of. This requires addition units in the industrial process.

A further disadvantage of the known catalysts is their capacity to promote the disproportionation of the organic compounds. For example, from monohydrogenated halocarbons (120 series) one obtains di- and zero hydrogenated halocarbons (130 series and 110 series or CFCs). This is particularly disadvantageous when the desired product be HFC-125, since among the 110 series there is formed CFC-115, which is extremly difficult to separate from 125 (see U.S. Pat. No. 5,087,329).

Other chromium and magnesium containing catalyst are known in the art: see e.g. U.S. Pat. No. 5,559,069 which refers to a catalyst containing Cr and Mg fluorides without any reference to the preparation of the 120 series. Moreover when the fluorination of an unsaturated starting material is carried out, the catalytic activity is very low and the selectivity is of no practical industrial interest.

In EP 417,680 it is described the preparation of 134a from 133a and HF in gaseous phase in the presence of an unsupported mixed catalyst based on Cr (III) and Mg, wherein the atomic ratio Cr/Mg is equal to or lower than 0.66.

Such catalyst is prepared according to the process described in U.S. Pat. No. 4,547,483, comprising the reaction of 1 mole of a Cr(III) soluble salt with at least 1.5 moles of Mg oxide or hydroxide in aqueous solution, with formation of a paste containing Cr hydroxide and Mg salt, which, after drying, is treated with HF at temperatures from 20° to 500° C.

It is stated that said coprecipitation method is unsuitable to the preparation of supported catalysts, and that Mg has the sole purpose to act as a binder, to confer to the catalyst the desired mechanical properties.

Said catalyst when employed under high pressures (5–15 bar) results particularly effective in reducing the amount of olefinic by-products and in particular that of $CF_2=CHCl$ (HCFC-1122) while if employed at atmospheric pressure it does not result effective in such reduction.

The use of high pressures implies however a greater cost of the fluorination industrial plants as regards the materials and the structural parts of the plant which must be not only resistant to high mechanical/chemical stresses but must meet more severe rule requirements meant to avoid possible risks of leakage of HF and of the reaction products.

EP 657,408 describes a fluorination process in gaseous phase with HF of halogenated aliphatic hydrocarbons, in particular of HCFC-133a in the presence of a mixed crystalline catalyst based on Cr oxide or oxides and at least another metal catalytically active selected from Ni, Co, Mn, Mg, Fe, Zn and V.

However such crystalline catalyst quickly deactivates in operation: for instance, a crystalline catalyst based on Mg $CrO_4$ and $Cr_2O_3$ deactivates after only 24 hour of operation.

BRIEF SUMMARY OF THE INVENTION

It has now been found a fluorination catalyst based on supported Cr (III) and Mg compounds which in the fluorination in the gaseous phase with HF of halogenated hydrocarbons carried out at atmospheric pressure allows to obtain high selectivity in the desired products, by reducing to a minimum the formation of olefinic by-products and moreover it results of a long life-time.

In particular, the fluorination catalyst according to the present invention resulted particularly suitable in the fluorination in gaseous phase with HF of HCFC-133a at atmospheric pressure, with obtainment of high selectivity (up to 99%) in HFC 134a, while reducing to a minimum the formation of the undesired HCFC-1122 and without suffering losses of activity for long operation periods (up to at least 10 days).

DETAILED DESCRIPTION OF THE INVENTION

An object of the present invention is therefore a fluorination catalyst based on an amorphous compound of Cr (III) and on a compound of another metal selected from Mg, Ca, Sr, Ba, Sc, Ti, Zr, wherein the atomic ratio Cr/other metal is comprised between 50:1 e 1:1, said compounds being supported on a support selected from $AlF_3$, $Al_2O_3$, fluorinated $Al_2O_3$ and carbon, said catalyst being prepared by impregnation of the support with a concentrated aqueous solution containing a soluble Cr (III) salt and a soluble salt of the other metal in a molar ratio from 1 to 50, and the so impregnated support, previously dried at 100–120° C., is treated with an inert gas flow at 300–400° C. for 5–15 hours and then activated with a flow of anhydrous HF at 300–400° C. for 15–30 hours.

By Cr(III) amorphous compound, a compound is meant which does not show cristallinity at the Rx diffraction analysis.

The other metal is preferably selected between Mg and Ca, more preferably is Mg.

The support is preferably $AlF_3$ or $Al_2O_3$ fluorinated for at least 90%, more preferably is $AlF_3$.

$AlF_3$ is preferably in the gamma and/or beta form.

The soluble salts of Cr (III) and of the other metal used in the impregnation are preferably selected from chlorides, nitrates and acetates, more preferably are chlorides.

The catalyst of the present invention is suitable for the fluorination of halogenated hydrocarbons, in particular of HCFC-133a, with HF in gaseous phase. For the preparation of HFC 134a the following are the preferred embodiments.

The atomic ratio Cr/other metal is preferably comprised between 4:1 and 20:1.

The amount of amorphous Cr (III) compound present in the catalyst is generally comprised between 5 and 15% by weight calculated as metal. As inert gas nitrogen is preferably employed.

The catalyst activation can be also carried out "in situ" in the same fluorination reactor with HF or with the mixture HF/organic reactants.

With the use of the catalyst according to the invention it is possible to carry out the fluorination of HCFC-133a to HFC-134a either at atmospheric pressure or at high pressure, by employing reaction temperatures from 250° C. to 450° C., preferably from 300° to 380° C.

In said fluorination results particularly suitable a catalyst, according to the invention, which consists of an amorphous Cr (III) compound and of a Mg compound in an atomic ratio Cr/Mg between 4:1 and 20:1, supported on $AlF_3$ and having a content in chromium from 6 to 12% by weight.

The above catalyst is furthermore suitable to the preparation of HCFC/HFC of the 120 series (in particular 123, 124, 125) with long life-time combined with both high selectivity and efficiency.

In the case of the 120 series one may operate both at atmospheric or superatmospheric pressure and in a preferred range of temperatures from 200° to 400° C., most preferably 250–350° C.

The atomic Cr/Mg ratio for the catalyst to be employed in the 120 series synthesis ranges preferably from 10/1 to 25/1; the preferred support is $AlF_3$ and the Cr content ranges from 6 to 12% by weight.

Some examples are given for illustrative purposes.

EXAMPLE 1 A

Preparation of a supported Cr/Mg catalyst with a Cr/mg atomic ratio of 5:1.

500 g of $AlF_3$, are impegnated with four portions of a 327 cc aqueous solution containing 327 g of $CrCl_3.6\ H_2O$ and 49.9 g of $MgCl_2.6\ H_2O$.

The so impregnated catalyst is treated with a nitrogen flow at 400° C. for 10 hours and successively with a HF flow at 360° C. for 24 hours.

The so obtained catalyst has a content of 9.5% by weight of chromium and of 0.9% by weight of magnesium and an atomic ratio Cr/Mg of 5:1.

EXAMPLE 1 B

Fluorination of HCFC-133a at 320° C.

220 g of the catalyst prepared in Example 1A, are placed into an Inconel 600 tubolar reactor, having a diameter of 50 mm, and heated to 320° C. in a nitrogen flow, then 95 g/hour of HF and 140 g/hour of HCFC-133a are fed, thus getting a contact time of 2.5 seconds and a molar ratio HF/133a of 4:1.

The reaction is carried out at 320° C. and at atmospheric pressure.

The contact time was calculated as ratio between the volume of the reactants at the reaction temperature and the apparent volume at rest of the catalyst bed.

The gases flowing out from the reactor are washed with water or with an alkaline aqueous solution to remove the acidity and then analysed by gas-liquid chromatography (GLC).

The conversion of 133a results to be of 12.1%, the selectivity in HFC-134a results 99.% and the content of HCFC-1122 results to be 0.04% by weight.

The conversion and the selectivity remain constant after 75 hours of operation.

EXAMPLE 1 C

Fluorination of HCFC-133a at 335° C.

The fluorination is continued in the same reactor containing the catalyst utilized for 75 hours in example 1B, but bringing the reaction temperature to 335° C. and slightly changing the flow-rates of the gaseous reactants HF and 133a so as to have the same contact time of 2.5 seconds and the same molar ratio HF/133a of 4:1.

A conversion of 133a of 14.2%, a selectivity in 134a of 98.9 and a content in HCFC-1122 of 0.09–0.1% by weight are obtained, whose values remain constant after further 95 hours (170 hours on the whole) of catalyst operation.

EXAMPLE 1 D

Fluorination of HCFC-133a at 350° C.

Fluorination of Example 1C is continued, but by raising the temperature to 350° C.

The conversion of 133a results of 17.5%, the selectivity in 134a results of 98.5% and the content in HCFC-1122 results to be 0.15% by weight.

After further 50 hours (220 hours on the whole) of catalyst operation, no differences in the obtained results were noticed.

EXAMPLE 1 E

Fluorination HCFC-133a at 375° C.

Fluorination of Example 1D is continued but by raising the temperature to 375° C.

The conversion of 133a results of 21%, the selectivity in 134a results of 97.5% and the content in HCFC-1122 of 0.25% by weight.

After further 30 hours (250 hours on the whole) of catalyst operation the conversion and the selectivity remain constant.

EXAMPLE 2 (COMPARATIVE)

The fluorination of 133a as in Examples 1B, 1C, 1D and 1E is carried out, but by utilizing a Cr catalyst free from magnesium prepared as in Ex. 1A without using the magnesium salt. The following results were obtained:

| EXAMPLES | 2B | 2C | 2D | 2E |
|---|---|---|---|---|
| Reaction temperatures | 320° C. | 335° C. | 350° C. | 375° C. |
| Initial conversion 133a % | 13.5–14 | 16 | 19.5 | 19.0 |
| Selectivity in 134a % | 98 | 98 | 97.2 | 95 |
| Content in HCFC-1122 % by weight | 0.18 | 0.2 | 0.25 | 0.5 |

The results obtained in Example 2B remain constant after 77 hours of operation.

The results of Example 2C remain constant after a total time of 146 hours.

The results of Example 2D remain constant up to 200 total hours, then the conversion begins to decay and after 220 total hours falls to 15%.

At the temperature of Example 2E the catalyst quickly decays and after 250 hours on the whole the conversion decreases to 13.3% and the selectivity results to be of 92%.

EXAMPLE 3A

Preparation of a catalyst with a Cr/Mg atomic ratio of 10:1

500 g of $AlF_3$ are impegnated with four portions of a 330 cc aqueous solution containing 329.5 g of $CrCl_3 \cdot 6H_2O$ and 26.9 g of $MgCl_2 \cdot 6H_2O$.

The so impregnated catalyst is treated with a nitrogen flow at 400° C. for 10 hours and successively with a HF flow at 360° C. for 24 hours.

The so obtained catalyst has a content of 10.5% by weight of Cr and 0.5% of Mg and a Cr/Mg atomic ratio of about 10.

EXAMPLE 3B

Fluorination of PCE at 300° C.

265 g (220 cc) of the catalyst of Ex. 1A are charged in an Inconel® 600 tubular reactor (diameter=50 mm) and heated to 300° C. in a nitrogen flow. Then the nitrogen is replaced by 56 g/h of anhydrous HF and 93 g/h of PCE, thus obtaining a 5 sec residence time and a HF/PCE mole ratio of 5/1.

The off-gases are scrubbed for the HF and HCl, dried and analysed by gas-chromatography (GC).

The PCE conversion results 45%, the combined selectivity of 120 series products is 98%, and in particular the 115/125 ratio is about 0.6%.

The following composition of the reaction products is representative:

| | % moles |
|---|---|
| $CF_3CHF_2$ (125) | 10.19 |
| $CF_3CHClF$ (124) | 11.71 |
| $CF_3CCl_2H + CF_2Cl-CHClF + CHF_2CCl_2F$ (123 + 123a + 123b) | 15.71 |
| $CHCl_2CCl_2F + CHCl_2CClF_2 + CClF=CCl_2$ (121 + 122 + 1111) | 5.08 |
| $CClF_2CF_3$ (115) | 0.06 |
| $CCl_2FCClF_2 + CClF_2CClF_2 + CClFCHF_2$ ecc. (113 + 114 + 133 + . . .) | 0.85 |
| PCE | 56.36 |

After 50 hours on stream both conversion and selectivity remain constant.

EXAMPLE 3C - Fluorination of PCE at 280° C.

The fluorination of Ex. 3A is continued, lowering the temperature to 280° C. (the reagent flow is slightly raised to maintain constant the residence time).

The following composition of the reaction products is representative:

| | % moles |
|---|---|
| $CF_3CHF_2$ (125) | 1.66 |
| $CF_3CHClF$ (124) | 7.04 |
| $CF_3CCl_2H + CF_2Cl-CHClF + CHF_2CCl_2F$ (123 + 123a + 123b) | 19.59 |
| $CHCl_2CCl_2F + CHCl_2CClF_2 + CClF=CCl_2$ (121 + 122 + 1111) | 7.72 |
| $CClF_2CF_3$ (115) | 0.01 |
| $CCl_2FCClF_2 + CClF_2CClF_2 + CClFCHF_2$ ecc. (113 + 114 + 133 + . . .) | 0.59 |
| PCE | 63.38 |

The conversion of PCE is about 35% and the 120 series selectivity is 98%. The 115/125 ratio is 0.4 ÷0.5%.

After 70 more hours on stream (120 hours total) the catalytic activity has a small lowering, the PCE conversion is about 30%.

EXAMPLE 4A - Fluorination of PCE with a Cr/Mg atomic ratio of 5:1

The same catalyst of Ex. 1A is used in the fluorination of PCE in the same conditions as in Ex. 3A.

The following composition is representative of the obtained products:

| | % moles |
|---|---|
| $CF_3CHF_2$ (125) | 0.66 |
| $CF_3CHClF$ (124) | 4.7 |
| $CF_3CCl_2H + CF_2Cl-CHClF + CHF_2CCl_2F$ (123 + 123a + 123b) | 17.1 |
| $CHCl_2CCl_2F + CHCl_2CClF_2 + CClF=CCl_2$ (121 + 122 + 1111) | 6.93 |
| $CClF_2CF_3$ (115) | <0.01 |
| $CCl_2FCClF_2 + CClF_2CClF_2 + CClFCHF_2$ ecc. (113 + 114 + 133 + . . .) | 0.76 |
| PCE | 69.88 |

EXAMPLE 5 - comparison

A catalyst is prepared as in Ex. 3A but without magnesium. This catalyst is employed in the fluorination of PCE in the same conditions of Ex. 3C.

The following results ar obtained:

|  | % moles |
|---|---|
| $CF_3CHF_2$ (125) | 1.0 |
| $CF_3CHClF$ (124) | 8.13 |
| $CF_3CCl_2H + CF_2Cl—CHClF + CHF_2CCl_2F$ (123 + 123a + 123b) | 22.4 |
| $CHCl_2CCl_2F + CHCl_2CClF_2 + CClF═CCl_2$ (121 + 122 + 1111) | 6.94 |
| $CClF_2CF_3$ (115) | 0.02 |
| $CCl_2FCClF_2 + CClF_2CClF_2 + CClFCHF_2$ etc. (113 + 114 + 133 + . . .) | 0.95 |
| PCE | 60.55 |

The activity and the overall selectivity are close to those of Exs. 3 and 4, but the 115/125 ratio is higher, 1÷1.5%.

But the catalyst deactivation is much faster: after 70 hours on stream nearly 40% of the initial activity is lost.

We claim:

1. A fluorination catalyst consisting of an amorphous Cr (III) compound and a compound of another metal selected from the group consisting of Mg, Ca, Sr, Ba, Sc, Ti and Zr, wherein the atomic ratio of Cr/other metal is between 50:1 and 1:1, said compounds being supported on an $AlF_3$ support and said catalyst being prepared by impregnation of the support with a concentrated aqueous solution containing a soluble Cr (III) salt and a soluble salt of the other metal in a molar ratio from 1 to 50, and the support thus impregnated is dried at 100–120° C., treated with an inert gas flow at 300–400° C. for 5–15 hours and then activated with an anhydrous HF flow at 300–400° C. for 15–30 hours.

2. A catalyst according to claim 1, wherein the "other metal" is Mg.

3. A catalyst according to claim 1, wherein the support is in the $AlF_3$ gamma and/or beta form.

4. A catalyst according to claim 1, wherein the soluble salts of Cr (III) and of the other metal are chlorides.

5. A catalyst according to claim 1, wherein the compound of another metal a is Mg compound and the atomic ratio Cr/Mg is between 4:1 and 20:1, and having a content in chromium from 6 to 12% by weight.

6. Process for the fluorination in gaseous phase of halogenated hydrocarbons with HF wherein a fluorination catalyst according to claim 1 is utilized.

7. Process according to claim 6, wherein 1,1,1,2-tetrafluoroethane is prepared by reacting in the gaseous phase 1,1,1,2-trifluoro-2-chloroethane with HF, at a temperature from 250° C. to 450° C.

8. Process according to claim 11, wherein the process is carried out at a temperature from 300° C. to 380° C.

9. Process according to claim 6, wherein 1,1,1-trifluoro-2,2-dichloroethane, 1,1,1,2-tetrafluoro-2-chloroethane and pentafluoroethane are prepared by reacting in the gaseous phase perchloroethylene with HF at a temperature from 250° C. to 350° C.

10. Process according to claim 6, wherein the process is carried out at a temperature from 200° C. to 400° C.

* * * * *